United States Patent [19]

Horwitz

[11] Patent Number: 5,108,745
[45] Date of Patent: Apr. 28, 1992

[54] TUBERCULOSIS AND LEGIONELLOSIS VACCINES AND METHODS FOR THEIR PRODUCTION

[75] Inventor: Marcus A. Horwitz, Los Angeles, Calif.

[73] Assignee: The Regents of the University of California, Berkeley, Calif.

[21] Appl. No.: 232,664

[22] Filed: Aug. 16, 1988

[51] Int. Cl.$^5$ .................... A61K 39/02; C12N 15/00
[52] U.S. Cl. ..................................... 424/92; 424/88; 435/172.1
[58] Field of Search .................. 435/172.1; 424/92, 88

[56] References Cited

U.S. PATENT DOCUMENTS

| | | | |
|---|---|---|---|
| 4,468,332 | 8/1984 | Peacock et al. | 210/755 |
| 4,514,509 | 4/1985 | Kohler et al. | 436/518 |
| 4,722,891 | 2/1988 | Drutz et al. | 435/7 |
| 4,780,407 | 10/1988 | Strosberg et al. | 435/7 |

OTHER PUBLICATIONS

Horwitz, Biological Abstracts, vol. 85(4):AB-495, Ref. No. 37619, 1988.

Conlan et al., Journal of General Microbiology, vol. 134, pp. 481-487, 1988.

"Purification and Characterization of an Extracellular Protease of *Legionella pneumophila*", Lawrence A. Dreyfus and Barbara H. Iglewski, Infection and Immunity, Mar. 1986, pp. 736-743.

"In Vitro Production of an Extracellular Protease by *Legionella pneumophila*", Michael R. Thompson, Richard D. Miller and Barbara H. Iglewski; Infection and Immunity, Oct. 1981, pp. 299-302.

"Interferon-γ-Activated Human Monocytes Inhibit the Intracellular Multiplication of *Legionella pneumophila*", Nina Bhardwaj, Thomas W. Nash and Marcus A. Horwitz, The Journal of Immunology, vol. 137, pp. 2662-2669, No. 8, Oct. 15, 1986.

"Interaction between the Legionnaires' Disease Bacterium (*Legionella pneumophila*) and Human Alveolar Macrophages", Thomas W. Nash, Daniel M. Libby and Marcus A. Horwitz; The American Society for Clinical Investigation, vol. 74, Sep. 1984, pp. 771-782.

"Activated Human Monocytes Inhibit The Intracellular Multiplication of Legionnaires' Disease Bacteria", Marcus A. Horwitz and Samuel C. Silverstein, J. Exp. Med., vol. 154, Nov. 1981, pp. 1618-1635.

"Enzymatic Activities of *Legionella pneumophila* and Legionella-like Organisms", Frederick S. Nolte, Gary E. Hollick and Richard G. Robertson, Journal of Clinical Microbiology, Jan. 1982, pp. 175-177.

Primary Examiner—Johnnie R. Brown
Assistant Examiner—Abdel A. Mohamed
Attorney, Agent, or Firm—Poms, Smith, Lande & Rose

[57] ABSTRACT

Vaccines and methods for their use in producing effective immune responses in mammalian hosts subsequently exposed to infection by intracellular pathogens including *Legionella pneumophila* wherein extracellular products of the pathogens are used as vaccines. After selecting a target intracellular pathogen, extracellular products of the selected pathogen which stimulate strong lymphocyte proliferative responses in immune hosts are then utilized as vaccines to immunize subsequent mammalian hosts to the target intracellular pathogen.

17 Claims, 1 Drawing Sheet

TUBERCULOSIS AND LEGIONELLOSIS VACCINES AND METHODS FOR THEIR PRODUCTION

REFERENCE TO GOVERNMENT

This invention was made with Government support under Grant No. AI-22421 awarded by the Department of Health and Human Services. The Government has certain rights in this invention.

FIELD OF THE INVENTION

The present invention relates in a broad aspect to vaccines against intracellular parasites. More specifically, the present invention relates to vaccines and methods for their use in producing an effective immune response in mammalian host animals subsequently exposed to infection by intracellular parasites such as *Leoionella pneumophila* wherein the extracellular products of such pathogens are used as vaccines rather than utilizing the surface components of such sequestered bacterial pathogens.

BACKGROUND OF THE INVENTION

Most bacteria are harmless. In fact, many are beneficial to man and to other mammalian animals. However, certain bacteria are able to grow and to spread in human and mammalian tissues. One class of such virulent organisms of particular interest is the intracellular pathogens. This category of virulent pathogens multiplies within the cells of the infected host organism rather than extracellularly.

The broad classification of intracellular pathogens includes organisms that are major causes of morbidity and fatality world-wide. For example, intracellular pathogens are responsible for the estimated 10,000,000 new cases of tuberculosis per year in the world (approximately 25,000 per year in the United States), the approximately 3,000,000 deaths per year from tuberculosis, and the estimated 12,000,000 cases of leprosy. They are also responsible for the estimated 10,000,000 cases of American trypanosomiasis (Chagas disease). Additionally, intracellular pathogens also cause other important diseases including cutaneous and visceral leishmaniasis, listeriosis, toxoplasmosis, histoplasmosis, trachoma, psittacosis, Q-fever, and Legionellosis including Legionnaires' disease. Few vaccines are available against such intracellular pathogen engendered diseases. The only widely used vaccine is BCG vaccine against tuberculosis. BCG vaccine is a live bacterial vaccine of questionable efficacy used primarily in Europe.

*Leoionella pneumophila* the causative agent of Legionnaires' disease is a particularly troublesome intracellular pathogen because it multiplies intracellularly in monocytes and macrophages, the very cells of the immune system intended to defend against it. Thus, *L. pneumophila* is in a class of intracellular pathogens which have actually circumvented the normal immune defenses by taking the cells of the immune system designed to kill bacteria and using them as host cells. Accordingly, *L. pneumophila* is particularly well suited to demonstrating the principles of the present invention.

Those skilled in the art will appreciate that the following exemplary discussion of *L. pneumophila* is in no way intended to limit the scope of the present invention to the treatment of Legionellosis or Legionnaires' disease alone and that the treatment of other intracellular pathogens is within the scope of the present invention.

The clinical investigation of Legionnaires' disease began in Jul. of 1976 when 221 people, mostly American Legionnaires' were struck with the disease in Philadelphia. Ultimately, 34 people lost their lives. Newly recognized, it was subsequently determined that Legionnaires' disease was not new and that it occurs world-wide in epidemic and endemic forms. It is believed to be a major cause of pneumonia in the United States and is responsible for a substantial proportion of fatal nosocomial pneumonia. Though affecting all age groups, it particularly affects those over 30 years of age, and targets men more often than women. The disease also demonstrates a predilection for individuals who smoke or abuse alcohol, travelers, construction workers, immunocompromised individuals and transplant patients. The case-fatality rate ranges between approximately 15%–20%.

*L. pneumophila* is an aerobic gram-negative bacterium with fastidious growth requirements. The organism is believed to be spread to humans and other mammalian hosts from contaminated sources by the airborne route. Ubiquitous in the environment, *L. pneumophila* has been isolated from water, soil, mud, and the cooling towers of air conditioning systems. It has also been associated with whirlpools and shower heads which can generate aerosols carrying the bacteria.

Human patients infected with this facultative intracellular bacterial pathogen develop both humoral and cell-mediated immune responses. Humoral immune responses appear to play only a secondary role in host defense against *L. pneumophila* because antibody does not promote killing of the bacterial pathogen by complement. Moreover, it promotes only modest killing by phagocytes and does not inhibit the intracellular multiplication of *L. pneumophila* in monocytes. Conversely, cell-mediated immune responses appear to play a primary role in host defenses against L. pneumophila because activated monocytes and alveolar macrophages inhibit its intracellular multiplication.

An excellent mammalian model for the study of Legionnaires' disease is the guinea pig which shares with humans a susceptibility to lung infection with *L. pneumophila*. After an incubation period of several days, guinea pigs exposed to aerosols containing L. pneumophila develop a pneumonic illness characterized by fever, weight loss, and labored respirations that sometimes culminates in death. This infectious syndrome closely parallels the clinical and pathological syndrome of Legionnaires' disease in humans. As with human patients, when exposed to a sublethal dose of *L. pneumophila*, guinea pigs also develop humoral and cell-mediated immune responses. Such guinea pigs also develop protective immunity to subsequent challenge with lethal doses of *L. pneumophila*. *L. pneumophila* is highly virulent for guinea pigs and is lethal to this animal by both the intraperitoneal and aerosol routes of inoculation.

Accordingly, for purposes of explanation only and not for purposes of limitation, the present invention will be discussed in the exemplary context of guinea pigs as the mammalian host. Those skilled in the art will appreciate that the present invention may be practiced with other mammalian hosts including humans.

It should be noted that *L. pneumophila* and other Legionella organisms are the causative agents for a variety of syndromes collectively referred to as "Legionellosis." In addition to Legionnaires' disease, Legionellosis includes Pontiac fever, Endocarditis and neurologic symptoms. Currently, no vaccine against Legionella engendered diseases exists. Moreover, as noted above, few vaccines exist against diseases caused by intracellular pathogens in general.

Compounding the search for effective vaccines against intracellular pathogens including *L. pneumophila* is the fact that these virulent pathogens are normally sequestered within cells of the host organism and thus are not readily detectable by the host's immune system. Moreover, with some intracellular pathogens, including *L. pneumophila*, antibodies produced against bacterial surface components actually induce uptake of the pathogens into the intracellular milieu they require to multiply. Accordingly, conventional vaccines which are traditionally directed against such bacterial cell surface antigens may actually stimulate the proliferation of these infectious organisms rather than resolving the infection. Thus, conventional vaccines directed against bacterial surface components may be contraindicated in the case of intracellular pathogens. Such conventional vaccines might be a particular problem for persons with depressed cell-mediated immunity, the form of immunity that primarily defends against infection with intracellular pathogens, because such persons would have diminished capacity to fight the more rapidly proliferating infection. Such persons include immunocompromised or immunosuppressed patients, such as organ transplant recipients or individuals infected with HIV, all of whom are particularly susceptible to infection with intracellular pathogens.

Accordingly, it is a principal object of the present invention to provide vaccines and methods for their use in mounting an effective immune response against intracellular pathogens such as *L. pneumophila*.

It is an additional object of the present invention to provide vaccines exhibiting reduced toxicity relative to traditional whole bacterial vaccines.

It is a further additional object of the present invention to provide vaccines and methods for their use which will not induce phagocytosis or cellular uptake of intracellular pathogens.

It is a still further additional object of the present invention to provide vaccines and methods for their use which will enable a vaccinated mammalian host to detect pathogens sequestered in host cells thereby allowing the host's immune system to kill or inhibit multiplication of the infecting pathogen.

SUMMARY OF THE INVENTION

These and other objects are achieved by the vaccines and method of the present invention which produce an effective immune response in mammalian hosts against subsequent infection by intracellular pathogens including various species and serogroups of *L. pneumophila*.

Briefly, the immunization method of the present invention utilizes extracellular products from such intracellular pathogens as immunizing agents rather than components of the pathogens themselves. Once immunized, these extracellular bacterial products are recognized by the host's immune system which can mount an effective immune response to subsequent infection by such pathogens.

In accordance with the teachings of the present invention effective mammalian vaccines against specific intracellular pathogens are produced by first selecting a target intracellular pathogen, identifying one or more extracellular products of the pathogen which stimulate strong lymphocyte proliferative responses in mammalian hosts which are immune to the target pathogen, and then immunizing hosts with the extracellular product.

An exemplary embodiment of the present invention utilizes the major secretory protein (MSP) of *L. pneumophila*. MSP is the major protein released into culture supernates during growth of *L. pneumophila* and induces a strong cell-mediated immune response in immunized mammals. MSP is easily obtained following growth of *Legionella pneumophila* in a laboratory broth.

More specifically, in an exemplary embodiment, *Legionella pneumophila*, Philadelphia 1 strain, is grown in yeast extract broth (albumin removed to facilitate MSP isolation) and the broth is centrifuged to pellet out the bacteria. The supernatant solution is retained and filtered and the MSP is precipitated from the supernatant through ammonium sulfate precipitation and then dialyzed. Further purification of the precipitated MSP is obtained through molecular sieve chromatography and subsequent ion exchange chromatography producing virtually 100% pure MSP.

Following purification, the MSP is administered, preferably through injection, to mammalian host animals either alone or with an adjuvant such as Freund's adjuvant or incomplete Freund's adjuvant. For example, immunization with purified MSP in complete Freund's adjuvant by subcutaneous injection followed by a second injection in incomplete Freund's adjuvant approximately 3 weeks later may be utilized. However, it is contemplated as being within the scope of the present invention to utilize a single administration of extracellular product where such compounds will induce an effective immune response to a target pathogen with a single dosage.

In one exemplary experiment, 5 guinea pigs were immunized as discussed above and 5 control guinea pigs were sham-immunized with complete and incomplete Freund's adjuvant lacking MSP. Three weeks later, both the test and control guinea pigs were challenged with a lethal dose of *Legionella pneumophila*. In the first experiment, 80% of the MSP immunized animals survived whereas 0% of the control animals survived. In a subsequent follow-up experiment, 83% of the MSP immunized animals survived while 0% of the control animals survived.

In the first experiment the animals received 10 micrograms of MSP in the first injection and 40 micrograms of MSP in the second injection. In the follow-up experiment the animals received 40 micrograms of MSP in both the first and the second injection.

Attesting to the breadth of the present invention, subsequent studies have proven that MSP extracted from the Philadelphia 1 strain of *Legionella pneumophila* has cross-reactivity between other serogroups and species of *Legionella*. Additionally, when fragmented through cyanogen bromide cleavage, MSP subunits continue to induce protective immunity. Similarly, MSP denatured through heat also continues to induce protective immunity.

Because it is believed that MSP and other secretory products of intracellular pathogens are released extracellularly by the infected host cells, the present invention enables the immune system of a vaccinated host to detect pathogens sequestered in the host's cells. In this manner, the vaccinated host's immune system is able to activate an effective immune response to kill or inhibit the multiplication of the pathogen inside it.

Equally important, antibodies directed against the extracellular secretory products do not induce uptake of the intracellular pathogen and therefore do not facilitate infection. This is particularly important for immunocompromised patients and organ transplant patients.

Other objects, features, and advantages of the present invention will be apparent to those skilled in the art from a consideration of the following detailed description of preferred exemplary embodiments thereof.

DETAILED DESCRIPTION

The present invention provides vaccines and methods for their use in developing effective immune responses to intracellular pathogens. As a preferred exemplary embodiment, Legionella pneumophila was utilized as the target pathogen. In accordance with the teachings of the present invention, MSP molecules that stimulated strong lymphocyte proliferative responses and cutaneous delayed-type hypersensitivity in immune (sublethally infected) guinea pigs were identified and then it was determined that immunization of guinea pigs with such molecules induced specific cell-mediated (and humoral) immune responses and protective immunity. Those skilled in the art will appreciate that the foregoing strategy can be utilized with any intracellular pathogen to practice the method of the present invention and, accordingly, the present invention is not specifically limited to vaccines and methods of immunization directed against L. pneumophila alone.

For example, following this strategy, MSP, the major secretory protein of L. pneumophila, was identified as being a molecule to which immune guinea pigs developed a very strong cell-mediated immune response. A simple three-step procedure for purifying large quantities of MSP was developed. Lymphocytes from immune animals were found to proliferate strongly in response to minute concentrations of MSP. Similarly, immune animals also developed a strong cutaneous delayed-type sensitivity to MSP. Guinea pigs subcutaneously immunized with MSP were studied for immune responses and it was determined that the MSP immunized guinea pigs developed strong specific cell-mediated immune responses (lymphocyte proliferation and cutaneous delayed-type sensitivity) to the MSP and, most importantly, developed effective immunity to lethal aerosol challenge with L. pneumophila.

In independent experiments, subcutaneous injection of guinea pigs with MSP provided 80%–100% protection against lethal aerosol challenge. Overall, 88% of 16 MSP immunized guinea pigs survived such challenge as compared to 0% of 15 control animals. In contrast to MSP, the two major components of Legionella pneumophila outer cell membrane, the lipopolysaccharide (dialyzed) and the major outer membrane protein, did not stimulate lymphocyte proliferation in immunized guinea pigs.

A further understanding of the present invention will be provided to those skilled in the art from the following non-limiting examples.

EXAMPLE 1

3-Step Purification of MSP from L. pneumophila

L. pneumophila is first passaged on Charcoal Yeast Extract Agar. Then the colonies are suspended from the agar in 10 ml Yeast Extract Broth (Equivalent to Albumin—Yeast Extract Broth without albumin). Two 2-liter sterile screw capped flasks are prepared, each with 500 ml Yeast Extract Broth. Each flask is prewarmed and inoculated with 5 ml of the L. pneumophila suspension, and incubated at 37° at 120 rpm overnight (approximately 20 hours). The purity of the culture is checked by light microscopy, scanning at least 10 fields at 400x, and by inoculating Sheep Blood Agar and Charcoal Yeast Extract Agar. (Most contaminants will grow rapidly (1 day) on both agars; L. pneumophila will grow slowly (several days) on Charcoal Yeast Extract Agar only). Aliquots of the broth are loaded into plastic centrifuge bottles and the bacteria are pelleted by centrifugation at 4° C. (In Sorvall Centrifuge with GAS rotor and 250 ml bottles, centrifuge at 12,000 rpm for 10 minutes). The supernatant fluid (containing MSP) is decanted and filtered through a 0.45 micron filter followed by 0.2 micron filter to remove any residual bacterial particles.

Ammonium sulfate is added to filtered supernatant fluid to 45% saturation at 4° C. with gentle stirring for 1 hour to precipitate non-MSP compounds. The solution is decanted to plastic bottles and the precipitate is pelleted by centrifugation at 4° C. (In RC5C Sorvall Centrifuge with GAS rotor and six 250 ml bottles, centrifuge at 12,000 rpm for 35 minutes.) The supernatant fluid is decanted and the 45% ammonium sulfate precipitate is discarded. Ammonium sulfate is added to the supernatant fluid to 95% saturation and the fluid is incubated at 4° C. with gentle stirring overnight. Following incubation, the solution is decanted to plastic bottles and the precipitate is pelleted by centrifugation as above. The supernatant fluid is discarded and MSP-rich precipitate is collected and washed twice with small volumes of BEN (0.025 M Bis Tris, 0.01 M EDTA, and 0.15 M NaCl, pH 5.9) and dialyzed in 5,000–6,000 mw spectapor dialysis membrane against 1 liter BEN at 4° C. overnight.

The dialyzed MSP-rich fluid is loaded on to a Sephacryl s-200, 50 cm ×2.5 cm column. (Equipment: LKB Multirac Fraction Collector, Beckman Model 153 Analytical UV Detector, Rabbit Peristaltic Pump (Rainin), Beckman Analytical Optical Unit, Linear Chart Recorder). The column is run at 8 ml/hour overnight and 2 ml fractions are collected and stored at 4. pending completion of the next step. 25 ul samples of each (or every other) fraction are examined by sodium dodecyl sulfate-polyacrylamide gel electrophoresis (SDS-PAGE). (25 ul of sample mixed with 25 ul sample buffer and loaded on 12.5% SDS-PAGE gel. Molecular weight standards run concurrently). Fractions containing the most amounts of MSP and least amount of non-MSP protein are identified and pooled. The pooled fractions are filter concentrated with an Amicon Filter Unit with a 30,000 molecular weight exclusion filter until volume is 2–4 ml.

The concentrated fractions are loaded onto a DEAE Sepharose CL-6B Column, (2.5 cm ×13 cm.). A gradient of 0.15 M NaCl to 0.65 M NaCl in 0.025 M Bis Tris, 0.01 M EDTA, pH 5.9, is applied using a gradient maker with 2.5 bed volumes in each chamber. The column is run at approximately 8 ml/hour and 2 ml fractions are collected and stored at 4° C. pending completion of the next step. 25 ul of each (or every other) fraction is examined by SDS-PAGE as above. Fractions containing only MSP are identified and pooled. The pooled volume is filter concentrated on ice with an Amicon Filter Unit with a 30,000 molecular weight exclusion filter until the volume is approximately 1 ml (per original liter of volume) The concentrate is then dialyzed in 5,000-6,000 MW Spectapor dialysis membrane against 3 changes of 1 liter BEN.

Figure 1:
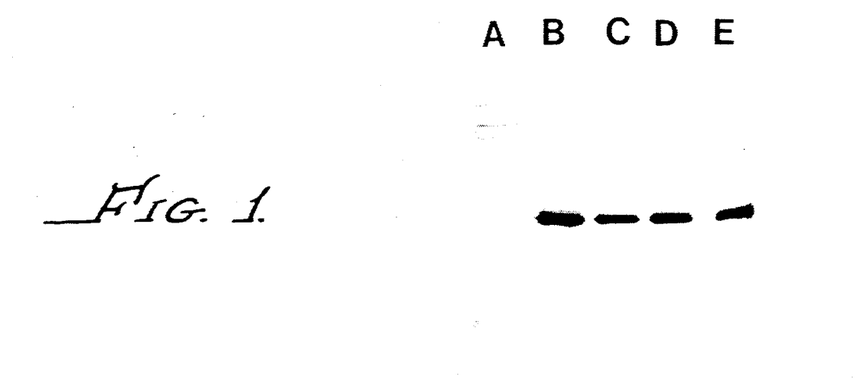
FIG. 1 shows the purification of MSP as identified by SDS-PAGE.

As shown in FIG. 1, *L. pneumophila* was grown in broth culture and the bacteria separated from the broth by centrifugation. The supernatant proteins were precipitated with ammonium sulfate and subjected to SDS-PAGE as discussed above. Lane B shows the protein profile of this preparation (Step 1). The proteins obtained after ammonium sulfate precipitation were applied to a molecular sieve column, fractions containing MSP were identified by SDS-PAGE, and the proteins in these fractions were ethanol precipitated and subjected to SDS-PAGE. Lane C shows the protein profile of this preparation (Step 2). The proteins obtained after molecular sieve chromatography were applied to an ion-exchange column, eluted, and examined by SDS-PAGE. Lane D shows the protein profile of this preparation (Step 3). Lane A contains molecular weight standards (bovine albumin, 66,000; ovalbumin, 45,000; glyceradlehyde -3- phosphate dehydrogenases 36,000; carbonic anhydrase, 29,000; trypsinogen, 24,000; trypsin inhibitor 20,100).

TABLE A

| Experiment | Status of Guinea Pigs | Number Guinea Pigs Surviving Per Number Challenged and % Survival | p* |
|---|---|---|---|
| A | Control | 0/5 (0%) | |
| | Immunized | 4/5 (80%) | 0.05 |
| B | Control | 0/5 (0%) | |
| | Immunized | 5/6 (83%) | 0.02 |
| C | Control | 0/4 (0%) | |
| | Immunized | 4/4 (100%) | 0.03 |
| D | Control | 0/6 (0%) | |
| | Immunized | 4/6 (67%) | 0.03 |
| TOTAL | Control | 0/20 (0%) | |
| | Immunized | 17/21 (81%) | 0.00000005 |

*Fisher's Extract Test, two-tailed

EXAMPLE 3

In two independent experiments, guinea pigs were immunized subcutaneously with MSP (40 ug in complete Freunds followed three weeks later by incomplete Freunds) or sham-immunized (complete Freunds only followed 3 weeks later by Incomplete Freunds only). All animals were skin tested with an intradermal injection of the indicated concentration of MSP in a total volume of 100 ul and the extent of erythema and induration measured 24 h later.

As shown in Table B, MSP-immunized animals exhibited marked erythema and induration in response to intradermal MSP in comparison to control animals, who had minimal responses.

TABLE B

| Experiment | Status of Guinea Pigs | Number of Guinea Pigs | Skin Reactions | Mean Extent of Erythema and Induration (mm) in Response to 100 ul of Indicated Concentration of MSP (ug/ml) | | | |
|---|---|---|---|---|---|---|---|
| | | | | 50 | 5 | 0.5 | 0 |
| A | Immunized | 6 | Erythema | 24 | 14 | 9 | 0 |
| | | | Induration | 13 | 7 | 4 | 0 |
| | Control | 3 | Erythema | 8 | 4 | 0 | 0 |
| | | | Induration | 0 | 0 | 0 | 0 |
| | | | S.I. (Erythema)* | 3 | 3.5 | ∞ | — |
| | | | S.I. (Induration)* | ∞ | ∞ | ∞ | — |
| | | | | 1 | 0 | | |
| B | Immunized | 3 | Erythema | 17 | 0 | | |
| | | | Induration | 6 | 0 | | |
| | Control | 3 | Erythema | 3 | 0 | | |
| | | | Induration | 1 | 0 | | |
| | | | S.I. (Erythema) | 5.7 | — | | |
| | | | S.I. (Induration) | 6.0 | — | | |

*S.I. = Mean skin reactivity (mm) mutant immunized guinea pigs/mean skin reactivity (mm) of control guinea pigs.

EXAMPLE 2

In four independent experiments, guinea pigs were immunized subcutaneously twice with 40 ug of MSP 3 weeks apart. The first dose was administered in complete Freunds and the second dose in incomplete Freunds. Control guinea pigs were sham-immunized with buffer in complete or incomplete Freunds. Three weeks later, all animals were challenged with a lethal aerosol dose of *L. pneumophila* and survival was quantitated.

As shown in Table A, immunized guinea pigs were strongly protected against lethal aerosol challenge.

EXAMPLE 4

In four independent experiments, guinea pigs were immunized with MSP or sham-immunized (Controls) as in the previous table. Splenic lymphocytes were obtained and incubated ($10^7$/ml) in microtest wells at 37° C. for 2 days without antigen, with MSP at the concentration indicated, with formalin-killed *L. pneumophila* (FKLP) ($10^8$/ml), or with L. pneumophila membranes ($10^8$/ml). The lymphocytes were then assayed for their capacity to incorporate $^3$H-thymidine, and stimulation indices calculated.

As shown in Table C, lymphocytes from MSP-immunized animals exhibited marked responses to MSP in comparison to lymphocytes from control animals. Lymphocytes from both MSP- immunized animals and control animals reacted weakly to formalin-killed *L. pneumophila* (FKLP) and *L. pneumophila* membranes.

TABLE C

| Experiment | Antigen | Stimulation Index *(S.I.) | | S.I. Immunized/ S.I. Control |
|---|---|---|---|---|
| | | Immunized Guinea Pigs | Control Guinea Pigs | |
| A | MSP (1 ug/ml) | 17.2 | 1.0 | 17.2 |
| | MSP (0.1 ug/ml) | 15.8 | 1.0 | 15.8 |
| | FKLP | 44.9 | 29.0 | 1.5 |
| | Membranes | 21.4 | 9.0 | 2.4 |
| B | MSP (1 ug/ml) | 13.8 | 1.2 | 11.5 |
| | MSP (0.1 ug/ml | 11.1 | 1.1 | 10.1 |
| | FKLP | 21.6 | 10.7 | 2.0 |
| | Membranes | 11.0 | 6.4 | 1.7 |
| C | MSP (10 ug/ml) | 15.2 | 7.7 | 2.0 |
| | MSP (1 ug/ml) | 4.2 | 5.5 | 0.8 |
| | FKLP | 28.5 | 28.3 | 1.0 |
| | Membranes | 34.4 | 26.3 | 1.3 |
| D | MSP (10 ug/ml) | 22.1 | 1.5 | 14.7 |
| | MSP (1 ug/ml) | 18.0 | 3.0 | 6.0 |
| | FKLP | 43.1 | 21.2 | 2.0 |
| | Membranes | 33.9 | 27.0 | 1.3 |

EXAMPLE 5

In two independent experiments, guinea pigs were immunized subcutaneously with MSP (40 ug in Complete Freunds) or sham-immunized (Controls) subcutaneously with Complete Freunds only. Three weeks later, splenic lymphocytes were obtained and incubated ($10^7$/ml) in microtest wells at 37° for two days without antigen, with MSP at the concentration indicated, or with heated MSP (60° C. ×1 hr.) at the concentration indicated. The lymphocytes were then assayed for their capacity to incorporate $^3$H-thymidine, and stimulation indices were calculated.

As shown in Table D, MSP-immunized guinea pigs exhibited marked lymphocyte proliferative responses to both MSP and heated (proteolytically inactive) MSP in comparison to control guinea pigs.

TABLE D

| Experiment | Antigen (ug/ml) | | Stimulation Indices (S.I.)* | | S.I. Immunized/ S.I. Control |
|---|---|---|---|---|---|
| | | | Immunized Guinea Pigs | Control Guinea Pigs | |
| A | MSP | (1) | 17.4 | 1.9 | 9.2 |
| | MSP | (0.1) | 17.5 | 3.9 | 4.5 |
| | Heated MSP | (1) | 11.2 | 2.0 | 5.6 |
| | Heated MSP | (0.1) | 8.8 | 3.6 | 2.4 |
| B | MSP | (1) | 24.7 | 1.9 | 13.0 |
| | MSP | (0.1) | 20.6 | 1.8 | 11.4 |
| | Heated MSP | (1) | 19.4 | 1.6 | 12.1 |
| | Heated MSP | (0.1) | 15.6 | 2.0 | 7.8 |

*Stimulation Index = (mean $^3$H-thymidine incorporation (cpm) of lymphocytes incubated with antigen)/(mean $^3$H-thymidine incorporation (CPM) of lymphocytes incubated without antigen).

EXAMPLE 6

In one experiment, a guinea pig was immunized with heated MSP (60° C. for 1 hour) subcutaneously (40 ug heated MSP in Complete Freunds followed 3 weeks later by ug heated MSP in Incomplete Freunds) and another guinea pig was sham-immunized (Control) subcutaneously (Complete Freunds only followed 3 weeks later by Incomplete Freunds only). Three weeks later, splenic lymphocytes were obtained and incubated ($10^7$/ml) in microtest wells at 37° C. for 2 days without antigen, with MSP at the concentration indicated, or with heated MSP at the concentration indicated. The lymphocytes were then assayed for their capacity to incorporate $^3$H-thymidine and stimulation indices were calculated.

As shown in Table E, lymphocytes from the guinea pigs immunized with heated, proteolytically inactive MSP exhibited a marked proliferative response to MSP at all concentrations and to 10 and 1 ug/ml heated MSP in comparison to lymphocytes from the control guinea pig.

TABLE E

| Experiment | Antigen (ug/ml) | | Stimulation Indices (S.I.)* | | S.I. Immunized/ S.I. Control |
|---|---|---|---|---|---|
| | | | Immunized Guinea Pig | Control Guinea Pig | |
| A | MSP | (10) | 19.8 | 5.1 | 3.9 |
| | MSP | (1) | 19.4 | 6.3 | 3.1 |
| | MSP | (0.1) | 10.4 | 0.9 | 11.6 |
| | MSP | (0.01) | 2.8 | 1.9 | 1.5 |
| | Heated MSP | (10) | 22.9 | 5.3 | 4.3 |
| | Heated MSP | (1) | 9.8 | 3.4 | 2.4 |
| | Heated MSP | (0.1) | 2.8 | 2.8 | 1.0 |

TABLE E-continued

| Experiment | Antigen (ug/ml) | Stimulation Indices (S.I.)* | | S.I. Immunized/ S.I. Control |
| --- | --- | --- | --- | --- |
| | | Immunized Guinea Pig | Control Guinea Pig | |
| | Heated MSP (0.01) | 1.4 | 1.2 | 1.2 |

*Stimulation Index = (mean $^3$H-thymidine incorporation (cpm) of lymphocytes incubated with antigen)/(mean $^3$H-thymidine incorporation (cpm) of lymphocytes incubated without antigen).

EXAMPLE 7

In two independent experiments, guinea pigs were immunized subcutaneously with MSP 40 ug in Complete Freunds followed three weeks later by 40 ug in Incomplete Freunds) or sham-immunized (Controls) subcutaneously (Complete Freunds only followed three weeks later by Incomplete Freunds only). Splenic lymphocytes were obtained and incubated ($10^7$/ml) in microtest wells at 37° C. for two days without antigen, with MSP at the concentration indicated, or with a Cyanogen Bromide digest of MSP (CNBr MSP) at the concentration indicated. The lymphocytes were than assayed for their capacity to incorporate $^3$-H-thymidine and stimulation indices were calculated.

As shown in Table F, lymphocytes from MSP immunized animals exhibited significantly stronger responses to MSP and to the higher concentration of CNBr than control animals.

TABLE F

| Experiment | Antigen (ug/ml) | Stimulation Index (S.I.)* | | S.I. Immunized/ S.I. Control |
| --- | --- | --- | --- | --- |
| | | Immunized Guinea Pigs | Control Guinea Pigs | |
| A | CNBr MSP 20** | 15.9 | 4.1 | 3.9 |
| | CNBr MSP 2** | 1.4 | 1.7 | 0.8 |
| | MSP 0.1 | 9.5 | 6.8 | 1.4 |
| B | CNBr MSP 20 | 12.7 | 3.0 | 4.2 |
| | CNBr MSP 2 | 1.7 | 1.5 | 1.1 |
| | MSP 0.1 | 12.9 | 3.6 | 3.6 |

*Stimulation Index = (mean $^3$H-thymidine incorporation (cpm) of lymphocytes incubated with antigen)/(mean $^3$H-thymidine incorporation (cpm) of lymphocytes incubated without antigen).
**Original amounts. Actual amounts in experiment likely lower because of losses with handling.

EXAMPLE 8

In two independent experiments, guinea pigs were immunized subcutaneously with MSP. 40 ug in Complete Freunds followed three weeks later by 40 ug in Incomplete Freunds) or sham-immunized (controls) subcutaneouslyu (Complete Freunds only). Splenic lymphocytes were obtained and incubated without antigen, or with the extracellular proteins of mutant L. pneumophila Philadelphia 1, L. pneumophila Togus 1, or L. pneumophilsChicago 2 at the concentrations indicated. Simulation indices were calculated.

As shown in Table G, lymphocytes from MSP Serogroup 1—immunized pigs exhibited a marked proliferative response to extracellular proteins of *L. pneumophila* Serogroups 1, 2, and 6 in comparison to control guinea pigs.

TABLE G

| Experiment | Strain | Serogroup | Concentration (ug/ml) of Extracellular Proteins | Stimulation Index (S.I.)* Immunized Guinea Pigs | Control Guinea Pigs | S.I. Immunized/ S.I. Control |
|---|---|---|---|---|---|---|
| A | Phil 1 | 1 | 20 | 12.8 | 4.0 | 3.2 |
| | (Mutant) | | 2 | 19.2 | 6.2 | 3.1 |
| | Togus 1 | 2 | 20 | 19.3 | 7.0 | 2.8 |
| | | | 2 | 15.8 | 6.8 | 2.3 |
| | Chicago 2 | 6 | 20 | 20.2 | 7.6 | 2.7 |
| | | | 2 | 11.7 | 6.4 | 1.8 |
| B | Phil 1 | 1 | 20 | 19.0 | 5.1 | 3.7 |
| | (Mutant) | | 2 | 17.0 | 6.9 | 2.5 |
| | Togus 1 | 2 | 20 | 21.4 | 7.0 | 3.1 |
| | | | 2 | 14.0 | 6.9 | 2.5 |
| | Chicago 2 | 6 | 20 | 12.8 | 8.2 | 1.6 |
| | | | 2 | 14.3 | 6.1 | 2.3 |

*S.I. = Mean skin reactivity (mm) mutant immunized guinea pigs/mean skin reactivity (mm) of control guinea pigs.

It should be noted that, as shown in FIG. 2, MSP from *L. pneumophila* Philadelphia 1 (Serogroup 1) shares common antigens with MSP-like molecules of the same apparent molecular weight from *L. pneumophila*Togus 1 (Serogroup 2), and L. pneumophila Chicago 2 (Serogroup 6), and a mutant derived from *L. pneumophila* Philadelphia 1. Total membranes of wild-type L. pneumophila Philadelphia 1 (Lane A), ammonium sulfate precipitated extracellular proteins of mutant *L. pneumophila* Philadelphia 1 (Lane B), *L. pneumophila Togus* 1 in Serogroup 2 (Lane C), *L. pneumophila* Chicago 2 in serogroup 6 (Lane D) and purified MSP from wild-type *L. pneumophila* Philadelphia 1 in Serogroup 1 (Lane E) were separated by SDS-PAGE and electrophoretically transferred onto nitrocellulose paper. The blots were then incubated with a 1:500 dilution of antiserum from a guinea pig immunized with purified MSP from wild-type *L. pneumophila* Philadelphia 1. The antigen-antibody complexes were revealed histochemically, using alkaline phosphatase —conjugated goat anti-guinea pig IgG.

Figure 2:
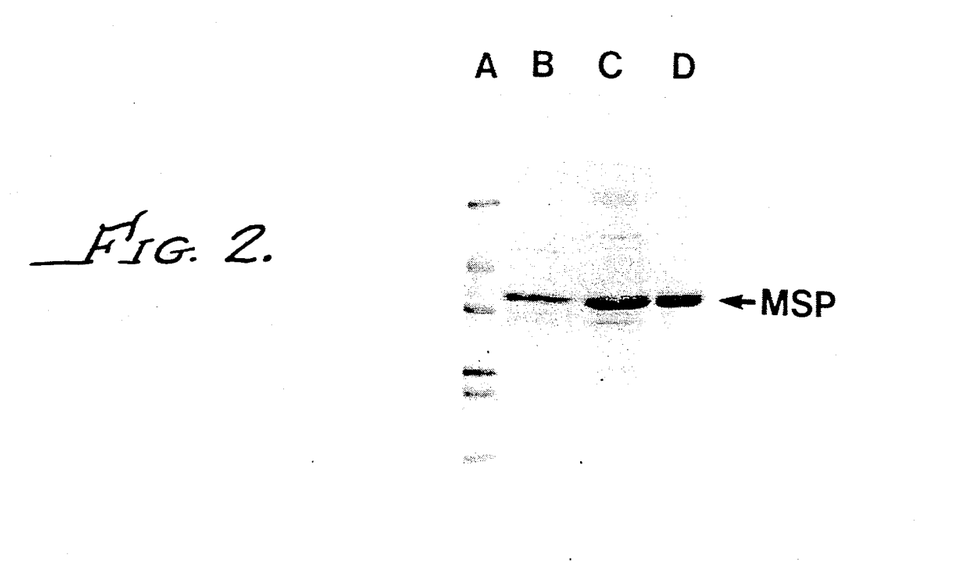
FIG. 2 shows the common MSP-like molecules shared by various serogroups of L. pneumophila.

The antibody against *L. pneumophila* Philadelphia 1 MSP (serogroup 1) not only recognized MSP of the wild-type (Lane E) and mutant (Lane B) *L. pneumophila* Philadelphia 1, but also an MSP-like molecule of *L. pneumophila* Togus 1 in Serogroup 2 (Lane C) and *L. pneumophila* Chicago 2 in Serogroup 6 (Lane D). The antibody did not detect any MSP in the membranes of wild-type *L. pneumophila* Philadelphia 1 (Lane A).

Because MSP may provide cross-protective immunity against challenge with other serogroups and species of *L. pneumophila*, those skilled in the art will appreciate that other species and serotypes of *Legionella* organisms may be utilized to practice the present invention with respect to vaccines directed against *L. pneumophila*. Accordingly, the forgoing examples are provided for purposes of illustration and are not intended to limit the scope and content of the present invention or to restrict this invention to MSP or vaccines against *Legionella pneumophila* alone or to particular species or serogroups thereof.

Those skilled in the art will appreciate further benefits of the present invention. For example MSP and other secretory or extracellular products are single types of molecules rather than whole bacteria, therefore less toxicity is likely to result from the vaccines of the present invention in contrast to known vaccines against intracellular organisms. Additionally, such extracellular products are easily obtained and purified and may also be produced synthetically through recombinant DNA technology and other techniques for the production of protein molecules known to those skilled in the art.

Further experiments with guinea pigs have indicated that an immunizing dosage as low as 10 micrograms of MSP will produce an effective immune response. Extrapolating on a per kilogram basis an exemplary human dosage of MSP as a vaccine against *L. pneumophila* would be on the order of 3 milligrams for a 70 kilogram individual.

Those skilled in the art will appreciate that the present invention may be embodied in other specific forms without departing from the spirit or essential attributes thereof. In that the foregoing description of the present invention discloses only preferred embodiments thereof, it is to be understood that other variations are contemplated as being within the scope of the present invention. Thus, by way of example, and not of limitation, the extracellular products of other intracellular parasites may be utilized to practice the present invention. Accordingly, the present invention is not limited to the particular embodiments which have been described in detail herein. Rather, reference should be made to the appended claims as indicating the scope and content of the present invention.

What is claimed is:

1. A method for producing human vaccine against *Legionella pneumophila*, said method comprising the steps of:
    identifying at least one extracellular product of *Legionella pneumophila* which stimulates strong cell mediated immune responses in at least one mammalian host infected with or immune to *Legionella pneumophila*; and
    determining a human protective immunity inducing effective amount of said extracellular product.

2. The method of claim 1 wherein said extracellular product is *Legionella pneumophila* major secretory protein.

3. Vaccine produced according to the method of claim 1.

4. A vaccinating agent for use in promoting an effective immune response to *Lecionella pneumophila* in mammals, said vaccinating agent comprising *Legionella pneumophila 1* major secretory protein.

5. The vaccinating agent of claim 4 wherein said major secretory protein is denatured.

6. The vaccinating agent of claim 4 wherein said major secretory protein is cleaved into smaller subunits.

7. The vaccinating agent of claim 4 wherein said major secretory protein is produced from *Legionella pneumophila* culture supernate.

8. The vaccinating agent of claim 4 wherein said major secretory protein is synthetically produced.

9. The vaccinating agent of claim 4 further comprising an adjuvant compound.

10. A method for immunizing a human host against subsequent exposure to *Legionella pneumophila*, said method comprising the step of immunizing said host with *Legionella pneumophila* major secretory protein.

11. The method of claim 10 wherein said major secretory protein is denatured.

12. The method of claim 10 wherein said major secretory protein is cleaved into smaller subunits.

13. A method for producing human vaccine against *Mycobacterium tuberculosis*, said method comprising the steps of:
    identifying at least one extracellular product of *Mycobacterium tuberculosis* which stimulates strong cell mediated immune responses in at least one mammalian host infected with or immune to *Mycobacterium tuberculosis*; and
    determining a human protective immunity inducing effective amount of said extracellular product.

14. Vaccine produced according to the method of claim 13 wherein said extracellular product is *Mycobacterium tuberculosis* major extracellular protein.

15. Vaccine produced according to the method of claim 13 wherein said intracellular pathogen is *Mycobacterium tuberculosis*.

16. A method for immunizing a human host against subsequent exposure to *Mycobacterium tuberculosis*, said method comprising the step of immunizing said host with *Mycobacterium tuberculosis* major extracellular protein.

17. A vaccinating agent for use in promoting an effective immune response to *Mycobacterium tuberculosis* in humans, said vaccinating agent comprising *Mycobacterium tuberculosis* extracellular protein.

* * * * *

REEXAMINATION CERTIFICATE (3561st)

United States Patent [19]
Horwitz

[11] B1 5,108,745
[45] Certificate Issued Jun. 30, 1998

[54] TUBERCULOSIS AND LEGIONELLOSIS VACCINES AND METHODS FOR THEIR PRODUCTION

[75] Inventor: Marcus A. Horwitz, Los Angeles, Calif.

[73] Assignee: The Regents of the University of California, Berkeley, Calif.

Reexamination Request:
No. 90/004,350, Sep. 3, 1996

Reexamination Certificate for:
Patent No.: 5,108,745
Issued: Apr. 28, 1992
Appl. No.: 232,664
Filed: Aug. 16, 1988

Certificate of Correction issued Jul. 27, 1993.

[51] Int. Cl.[6] .................. A61K 39/02; A61K 39/04; C12N 15/00
[52] U.S. Cl. ..................... 424/234.1; 435/172.1
[58] Field of Search ................. 424/234.1; 435/172.1

[56] References Cited

U.S. PATENT DOCUMENTS

4,689,397   8/1987   Shinnick et al. .................. 530/327

OTHER PUBLICATIONS

Thompson et al. "In Vitro Production of an Extracellular Protease by *Legionella pneumophila*" Inf. Immun., 34(1):299–302, 1981.

American Federation for Clinical Research Abstracts, vol. 35, No. 3 (1987).

*Primary Examiner*—James C. Housel

[57] ABSTRACT

Vaccines and methods for their use in producing effective immune responses in mammalian hosts subsequently exposed to infection by intracellular pathogens including Legionella pneumophila wherein extracellular products of the pathogens are used as vaccines. After selecting a target intracellular pathogen, extracellular products of the selected pathogen which stimulate strong lymphocyte proliferative responses in immune hosts are then utilized as vaccines to immunize subsequent mammalian hosts to the target intracellular pathogen.

B1 5,108,745

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–17 is confirmed.

* * * * *